US005519162A

United States Patent [19]

Agarwal et al.

[11] Patent Number: 5,519,162

[45] Date of Patent: May 21, 1996

[54] METHOD FOR REMOVING A HYDROGEN CYANIDE CONTAMINANT FROM AN ORGANIC LIQUID

[75] Inventors: Sudhir K. Agarwal; Rajiv M. Banavali, both of Houston; Bharati D. Chheda, Spring; Samuel F. Reed, Jr., Seabrook, all of Tex.

[73] Assignee: Rohm and Haas Company, Philadelphia, Pa.

[21] Appl. No.: 294,526

[22] Filed: Aug. 23, 1994

[51] Int. Cl.$^6$ ......................... C07C 253/34; C07C 67/48; C07C 69/06

[52] U.S. Cl. .......................... 560/248; 558/463; 558/435; 558/411; 560/218; 568/699; 568/920

[58] Field of Search .................................... 560/248, 218; 568/920, 699; 585/800; 558/463

[56] References Cited

U.S. PATENT DOCUMENTS 3,821,220 6/1974 Daugherty et al. .................. 260/249.6

4,131,642 12/1978 Miller et al. ........................ 562/609 X

OTHER PUBLICATIONS

Metal/Cyanide–Containing Wastes, Treatment Technologies by S. A. K. Palmer, M. A. Breton, T. J. Nunno, D. M. Sullivan, N. F. Surprenant, Alliance Technologies Corporation, Pollution Technology Review No. 158; 1988; [1 page only–presented and considered–p. 26].

EPA Methods For Chemical Analysis Of Water And Wastes, pp. 335.1–1–335.1–2 [1974].

*Primary Examiner*—Joseph Paul Brust

*Attorney, Agent, or Firm*—Darryl P. Frickey; Thomas J. Howell

[57] ABSTRACT

A method for removing hydrogen cyanide from a hydrogen cyanide-contaminated organic liquid includes the steps of contacting the hydrogen cyanide-contaminated organic liquid with a metal alkoxide to generate a metal cyanide salt and an alkanol and then separating the organic liquid from the metal cyanide salt and the alkanol.

6 Claims, No Drawings

METHOD FOR REMOVING A HYDROGEN CYANIDE CONTAMINANT FROM AN ORGANIC LIQUID

The present invention relates to a method for removing a hydrogen cyanide contaminant from an organic liquid.

Hydrogen cyanide is used or generated as a by-product in a variety of commercially significant chemical processes. The presence of even trace amounts of hydrogen cyanide in a product poses safety hazards with respect to toxicity and flammability. Furthermore, use of hydrogen cyanide-contaminated products may ultimately lead to accumulation of hydrogen cyanide in the headspace of product storage vessels and in aqueous environments, e.g., ground water. Processes for detection of hydrogen cyanide in waste waters and for removal of hydrogen cyanide from waste waters are known, see e.g., EPA Methods for Chemical Analysis of Water and Wastes, Method 335.1 and Palmer, S., Breto, M., Nunno, T., Sullivan, D., and Surprenant, N., "Metal/Cyanide Containing Wastes- Treatment Technologies", Pollution Technology Review No. 158, 1988, Noyes Data Co., Park Ridge, N.J. While some processes of limited applicability, see, e.g., U.S. Pat. No. 3,821,220 which discloses a method for reducing the level of hydrogen cyanide in triazines by treatment with formaldehyde, are known, satisfactory and broadly applicable methods for detection of low levels of hydrogen cyanide impurities in organic liquids and for removing hydrogen cyanide impurities from organic liquids have not been developed.

A first aspect of the present invention concerns a method for removing hydrogen cyanide contaminant from a hydrogen cyanide-contaminated organic liquid. The method includes the steps of contacting the hydrogen cyanide-contaminated organic liquid with a metal alkoxide to generate a metal cyanide salt and an alkanol and then separating metal cyanide salt and the alkanol from the organic liquid. The method of the present invention allows reduction of the amount of hydrogen cyanide in a hydrogen cyanide-contaminated organic liquid to selected levels which range down to below the limit of detection, i.e., to below about 50 parts per billion (ppb).

A second aspect of the present invention concerns a method for detecting low level of hydrogen cyanide in a liquid phase or gas phase organic compound. A sample to be analyzed for hydrogen cyanide content is separated into discrete components in a gas chromatograph and the nitrogen content of the components is detected using a nitrogen-phosphorus detector.

The method of the present invention is applicable to those hydrogen cyanide-contaminated organic liquids wherein the organic liquid itself is not reactive with the metal alkoxide under the treatment conditions used. Suitable organic liquids include, for example, alkanes such as, for example, pentanes, hexanes, heptanes and octanes, alkenes such as, for example, propylene, butylene, isobutylene, alkene oligomers, alcohols such as, for example, methanol and ethanol, isopropanol, butanol, octanol, esters such as, for example, formates, acetates and benzoates, aromatic compounds such as, for example, toluene, benzene and xylenes, ethers such as, for example, diethyl ether and dibutyl ether, and ethylenically unsaturated monomers such as, for example, methyl methacrylate and acrylonitrile, and nitriles, such as, for example, acetonitrile and benzonitrile.

In a preferred embodiment, the hydrogen cyanide-contaminated organic liquid initially contains up to about 50,000 ppm (parts per million) hydrogen cyanide and, more preferably, initially contains from about 500 ppm hydrogen cyanide to about 10,000 ppm hydrogen cyanide.

The hydrogen cyanide-contaminated organic liquid to be treated according to the method of the present invention may also include water as a secondary contaminant and the method provides an additional advantage with respect to the treatment of such liquids in that the method has also been found to reduce the water content of water-contaminated organic liquids.

In a preferred embodiment, the metal alkoxide is a compound of the structural formula (1):

$$M\text{-}(O\text{—}R_1)_n \qquad (1)$$

wherein:

M is a metal cation;

$R_1$ is $(C_1–C_{10})$alkyl; and n is an integer from 1 to 4.

As used herein, the terminology "metal cation" means a metal ion having a positive charge, such as, e.g., positively charged ions of zinc, titanium, sodium, potassium, lithium, aluminum, silicon and antimony.

The term "$(C_1–C_{10})$alkyl" means a straight-chain or branched alkyl group having from 1 to 10 carbon atoms per group, including, for example, methyl, ethyl, n-butyl, t-butyl, t-pentyl, heptyl, nonyl. Preferably, $R_1$ is $(C_1–C_6)$alkyl.

Suitable metal alkoxides include, for example, sodium methoxide, potassium ethoxide, lithium t-butoxide, potassium t-butoxide, sodium t-pentoxide, triisopropoxy titanate and tetramethoxy silane. Mixtures of metal alkoxides are also suitable. In a highly preferred embodiment, the metal alkoxide is sodium methoxide or potassium t-butoxide.

Polymeric metal alkoxides, such as, for example, poly-(dimethoxy siloxane), poly(dibutyl titanate) and poly(antimony ethylene glycoside) are also suitable as the metal alkoxide.

In a preferred embodiment, the metal alkoxide is generated by treating a metal with excess alcohol to form a solution of the metal alkoxide in the alcohol, for example, by treating sodium with excess methanol to form solution of sodium methoxide in methanol. Suitable alcoholic solutions of metal alkoxides may be generated using one or more metal compounds in combination with one or more alcohols.

The hydrogen cyanide-contaminated organic liquid is contacted with the metal alkoxide, for example, by agitating a mixture of the hydrogen cyanide-contaminated organic liquid and the metal alkoxide or by passing the organic liquid through a fixed or fluidized bed comprising the metal alkoxide.

In a preferred embodiment, the hydrogen cyanide-contaminated organic liquid is contacted with the metal alkoxide by agitating a mixture of the hydrogen cyanide-contaminated organic liquid and the metal alkoxide.

In a preferred embodiment, the metal alkoxide is introduced into the hydrogen cyanide-contaminated organic liquid as a solution of the metal alkoxide in an organic solvent or a mixture of organic solvents. Suitable organic solvents are those that are either identical to the organic liquid to be treated or miscible with and readily separable, for example, by distillation, from the organic liquid to be treated. Suitable organic solvents include, for example, methanol, ethanol, tetrahydrofuran and diethyl ether.

In a highly preferred embodiment, the metal alkoxide is introduced into the organic liquid to be treated as a solution in an organic solvent that is identical to the organic liquid to be treated.

In a first alternative highly preferred embodiment, solid phase metal alkoxide is added directly to the hydrogen cyanide-contaminated organic liquid.

In a second alternative highly preferred embodiment, the metal alkoxide is introduced into the hydrogen cyanide-contaminated organic liquid as a solution of the metal alkoxide in its corresponding alcohol.

In a preferred embodiment, the hydrogen cyanide-contaminated organic liquid is contacted with an excess, based on the molar amount of hydrogen cyanide contaminant in the liquid, of the metal alkoxide. In a highly preferred embodiment, the hydrogen cyanide-contaminated organic liquid is contacted with an molar excess of about 10% to about 300% of the metal alkoxide, based on the moles of hydrogen cyanide contaminant initially contained in the organic liquid to be treated.

In a preferred embodiment, the hydrogen cyanide-contaminated organic liquid is contacted with the metal alkoxide at a temperature from about 0° C. to about 100° C., more preferably from about 20° C. to about 60° C.

The hydrogen cyanide-contaminated organic liquid is contacted with the metal alkoxide for a period of time that is effective under the treatment conditions to allow conversion of the hydrogen cyanide contaminant into a metal cyanide salt and an alkanol. The contact time required is dependent upon the treatment temperature, the initial level of hydrogen cyanide contaminant contained in the organic liquid, the amount of metal alkoxide used and the target level of hydrogen cyanide in the purified organic liquid. In a preferred embodiment, the mixture of hydrogen cyanide-contaminated organic liquid and metal alkoxide is contacted for a time period of about 1 minute to about 4 hours, more preferably, from about 5 minutes to about 1 hour.

Subsequent to conversion of the hydrogen cyanide contaminant to a metal cyanide salt and an alkanol, the organic liquid is separated, e.g., by distillation, liquid-liquid extraction or filtration, from the metal cyanide salt and the alkanol, as well as from any organic solvent used to introduce the metal alkoxide, to provide a purified organic liquid. The appropriate separation method is selected in a known way based on the respective physical and chemical properties of the particular compounds to be separated.

In a preferred embodiment, the metal alkoxide-treated organic liquid is distilled to provide the purified organic liquid.

In a preferred embodiment of the hydrogen cyanide detection method of the present invention, the amount of hydrogen cyanide contained in a sample of hydrogen cyanide-contaminated organic liquid is quantified. A relationship between the nitrogen content of the liquid as detected by the method and the hydrogen cyanide content of the liquid is developed for a particular organic liquid by conducting the steps of separating and detecting on each of a series of samples of the organic liquid, wherein each of the samples has a respective known hydrogen cyanide content.

A sample having an unknown hydrogen cyanide content is then separated into components in a gas chromatographic column and the nitrogen content of the components of the sample having an unknown hydrogen cyanide content is detected using a nitrogen-phosphorus detector. The hydrogen cyanide content of a sample having an unknown hydrogen cyanide content is then quantified by comparing the nitrogen content detected for the sample having an unknown hydrogen cyanide content to the relationship between hydrogen cyanide content and nitrogen content detected.

The detection method of the present invention provides quantitative results in the range of about 50 ppb hydrogen cyanide to about 100 ppm hydrogen cyanide and indicates the presence of hydrogen cyanide by providing a qualitative response in the range of about 10 ppb hydrogen cyanide to about 50 ppb hydrogen cyanide.

EXAMPLE 1

Each of the compositions of Examples 1A–1G were made by dissolving a known amount of hydrogen cyanide in methyl formate.

The hydrogen cyanide content of each of the compositions of Examples 1A–1G was then measured using the following method:

An HP 5890 Gas Chromatograph (Hewlett-Packard) equipped with a HP-FFAP crosslinked, 0.2 mm diameter, 25 meter long fused silica capillary column having a 0.3 micrometer film thickness (Hewlett-Packard) and a split/splitless injector was used to separate the sample and a Nitrogen-Phosphorous detector (Hewlett-Packard Part No. 19234-60560) was used to detect the level of nitrogen in the column effluent.

The injector and detector were each run at 150° C. Helium was used as the carrier gas at a flow rate of from 1 milliliter to 4 milliliters per minute. A 1 microliter sample size was used for the determinations of liquid phase hydrogen cyanide content. A 1 milliliter sample size was used for the determinations of gas phase hydrogen cyanide content in the headspace over the liquid sample.

The apparatus was calibrated using a serial dilution of hydrogen cyanide in methyl formate. A plot of detector response versus hydrogen cyanide content gave a linear relationship having a correlation coefficient of greater than 0.99 (least squares fit) in the range of 50 ppb hydrogen cyanide to 100 ppm hydrogen cyanide.

The gas phase hydrogen cyanide content in the headspace above each of a series of samples of known solutions of hydrogen cyanide in methyl formate was then measured and correlated with liquid phase hydrogen cyanide content to demonstrate the reduction in gas phase hydrogen cyanide content provided by the process of the present invention.

Results of the gas phase analysis are set forth in TABLE 1, as the measured liquid phase hydrogen cyanide content ($HCN_l$ measured) and the measured gas phase hydrogen cyanide content ($HCN_g$ measured) each expressed in parts per million (ppm), for each of the compositions of Examples 1A–1G. The notation "ND" is entered to indicate that the hydrogen cyanide content of the sample was below the limit of detection using the above-disclosed method for measuring gas phase hydrogen cyanide content.

TABLE 1

| Ex # | $HCN_l$ measured (ppm) | $HCN_g$ measured (ppm) |
|---|---|---|
| 1A | 0 | ND |
| 1B | 0.5 | ND |
| 1C | 5 | 1.6 |
| 1D | 10 | 3.3 |
| 1E | 15 | 5 |
| 1F | 50 | 16 |
| 1G | 100 | 33 |

EXAMPLES 2–25

The contaminated organic liquid compositions of Examples 2–25 were each made by adding a known amounts of hydrogen cyanide to a respective sample of an organic liquid. The initial hydrogen cyanide content of the composition was measured according to the method set forth above in Example 1. The initial water content of some of the compositions was measured by Karl-Fisher titration.

Each of the hydrogen cyanide-contaminated compositions was introduced into a 3-necked round-bottomed flask equipped with a Vigreux column, a condenser and a receiving flask. A metal alkoxide was then added to the flask, as either a solid or as a solution in an organic solvent, to provide a desired molar ratio of metal alkoxide to hydrogen cyanide in the flask. The contents of the flask were then agitated vigorously for 10 minutes at room temperature. Following the period of agitation, the contents of the flask were distilled to provide a purified organic liquid. The hydrogen cyanide content of the purified liquid was then determined by the method set forth above in Example 1. The water content of some of the purified liquids was measured by Karl-Fisher titration.

Results are set forth in TABLE 2, as the organic liquid used, the initial hydrogen cyanide concentration of the contaminated liquid (($HCN_i$), the initial water content of the contaminated liquid ($Water_i$), the metal alkoxide used, the molar ratio of metal alkoxide to hydrogen cyanide, the hydrogen cyanide concentration of the purified liquid ($HCN_f$) and the water content of the purified liquid ($Water_f$), with each of the hydrogen cyanide concentrations being expressed in parts per million (ppm) and each of the water content values being expressed as a weight percent (wt. %), for each of the compositions of Examples 2–22. The notation "ND" is entered to indicate that the hydrogen cyanide content of the sample was below the limit of detection using the above-disclosed method for measuring gas phase hydrogen cyanide content.

The entries in the metal alkoxide column each bear a superscript that indicates the form in which the metal alkoxide was introduced into the liquid to be treated:

- a superscript "1" indicates that the metal alkoxide was introduced as a solid;
- a superscript "2" indicates that the metal alkoxide was introduced as a 25 wt. % solution in methanol;
- a superscript "3" indicates that the metal alkoxide was introduced as a 1 molar solution in methanol;
- a superscript "4" indicates that the metal alkoxide was introduced as a 21 wt. % solution in ethanol;
- a superscript "5" indicates that the metal alkoxide was introduced as a 1 molar solution in tetrahydrofuran; and
- a superscript "6" indicates that the metal alkoxide was introduced as a 1 molar solution in diethyl ether.

TABLE 3

| EX # | Liquid | $HCN_i$ (ppm) | $Water_i$ (wt %) | Metal Alkoxide | Molar Ratio | $HCN_f$ (ppm) | $Water_f$ (wt %) |
|---|---|---|---|---|---|---|---|
| 2 | methyl formate | 1008 | — | sodium methoxide[2] | 1.31 | 0.42 | — |
| 3 | methyl formate | 1008 | — | sodium methoxide[2] | 1.4 | 0.4 | — |
| 4 | methyl formate | 1008 | 0.3 | sodium methoxide[2] | 2.0 | 0.15 | — |
| 5 | methyl formate | 1008 | — | sodium methoxide[3] | 2.65 | 1.05 | — |
| 6 | methyl formate | 1099 | — | sodium methoxide[4] | 10 | ND | — |
| 7 | methyl formate | 1150 | — | sodium ethoxide[4] | 2 | 0.2 | — |
| 8 | methyl formate | 1150 | — | sodium methoxide[1] | 2 | 0.9 | — |
| 9 | methyl formate | 1024 | — | potassium methoxide[1] | 2 | 81.2 | — |
| 10 | methyl formate | 1024 | — | lithium methoxide[3] | 2 | 21 | — |
| 11 | methyl formate | 10245 | — | sodium t-pentoxide[1] | 2 | 0.16 | — |
| 12 | methyl formate | 1008 | 0.3 | potassium t-butoxide[5] | 3 | ND | 0.1 |
| 13 | methyl formate | 1012 | — | methyl lithium[6] | 1.79 | 129 | — |
| 14 | methanol | 1122 | 0.09 | sodium methoxide[2] | 2 | 18 | 0.05 |
| 15 | ethanol | 1033 | 9.1 | sodium methoxide[1] | 2 | 1029 | 8.2 |
| 16 | ethyl acetate | 1055 | 0.1 | sodium methoxide[2] | 2 | 6.8 | ND |
| 17 | ethyl formate | 1046 | 0.12 | sodium methoxide[2] | 2 | 52.8 | 0.09 |
| 18 | heptane | 800 | 0.1 | sodium methoxide[2] | 2 | 9.8 | 0.01 |
| 19 | toluene | 1092 | 0.8 | sodium methoxide[2] | 2 | 102.6 | 0.01 |
| 20 | acrylo-nitrile | 1072 | 0.6 | sodium methoxide[1] | 2 | 0.05 | ND |
| 21 | acrylo-nitrile | 1072 | 0.6 | potassium t-butoxide[5] | 2 | ND | ND |
| 22 | methyl meth-acrylate | 1196 | 0.31 | sodium methoxide[1] | 2 | 0.05 | ND |
| 23 | diiso-butylene | 1135 | 0.1 | sodium methoxide[1] | 2 | 1.5 | ND |
| 24 | dibutyl | 1153 | 0.1 | sodium | 2 | 0.05 | 0.1 |

TABLE 3-continued

| EX # | Liquid | $HCN_i$ (ppm) | $Water_i$ (wt %) | Metal Alkoxide | Molar Ratio | $HCN_f$ (ppm) | $Water_f$ (wt %) |
|---|---|---|---|---|---|---|---|
| | ether | | | methoxide[1] | | | |
| 25 | methyl formate | 25,000 | — | sodium methoxide[1] | 2 | 0.2 | — |

The method of the present invention allows reduction of the amount of hydrogen cyanide in a hydrogen cyanide-contaminated organic liquid to selected levels which range down to below the limit of detection, i.e., to below about 10 ppb hydrogen cyanide, and allows reduction of the water content of a water-contaminated organic liquid.

We claim:

1. A method for removing hydrogen cyanide from a hydrogen cyanide-contaminated organic liquid, comprising:

contacting the hydrogen cyanide-contaminated organic liquid with a metal alkoxide to generate a metal cyanide salt and an alkanol comprising agitating a mixture of the hydrogen cyanide-contaminated organic liquid and the metal alkoxide or passing the organic liquid through a fixed or fluidized bed comprising the metal alkoxide; and separating the organic liquid from the metal cyanide salt and the alkanol comprising distilling, liquid-liquid extracting or filtering the organic liquid; wherein the hydrogen cyanide-contaminated organic liquid is contaminated with up to about 50,000 parts per million hydrogen cyanide; wherein the organic liquid itself is not reactive with the metal alkoxide used and the organic liquid contains less than about 129 parts per million hydrogen cyanide subsequent to the steps of contacting and separating; and wherein the metal alkoxide is a compound of the structural formula:

$$M-(O-R_1)_n$$

wherein:

M is a metal cation selected from one or more of zinc, titanium, sodium, potassium, lithium, aluminum, silicon and antimony;

$R_1$ is $(C_1-C_{10})$alkyl; and n is an integer from 1 to 4.

2. The method of claim 1, wherein the organic liquid is selected from the group consisting of alkanes, alkenes, esters and aromatic hydrocarbyl compounds.

3. The method of claim 1, wherein the organic liquid is contaminated with from about 500 parts per million hydrogen cyanide to about 10,000 parts per million hydrogen cyanide.

4. The method of claim 3, wherein the organic liquid contains less than about 10 parts per million hydrogen cyanide subsequent to the steps of contacting and separating.

5. The method of claim 1, wherein the metal alkoxide is selected from the group consisting of sodium methoxide and potassium t-butoxide.

6. The method of claim 1, wherein the organic liquid is contacted with an molar excess of about 10% to about 300% of the metal alkoxide, based on moles of hydrogen cyanide contaminant initially contained in the liquid.

* * * * *